United States Patent [19]
Familoni

[11] Patent Number: 6,083,249
[45] Date of Patent: *Jul. 4, 2000

[54] APPARATUS FOR SENSING AND STIMULATING GASTROINTESTINAL TRACT ON-DEMAND

[75] Inventor: Babajide O. Familoni, Cordova, Tenn.

[73] Assignee: Medtronic, Inc., Minneapolis, Minn.

[*] Notice: This patent is subject to a terminal disclaimer.

[21] Appl. No.: 09/161,430

[22] Filed: Sep. 24, 1998

Related U.S. Application Data

[63] Continuation-in-part of application No. 08/846,783, Apr. 30, 1997, Pat. No. 5,861,014.

[51] Int. Cl.$^7$ .................................................. A61N 1/36
[52] U.S. Cl. ............................................................. 607/40
[58] Field of Search ................................ 607/40, 133, 41

[56] References Cited

U.S. PATENT DOCUMENTS

| | | |
|---|---|---|
| 4,981,470 | 1/1991 | Bombeck, IV . |
| 5,188,104 | 2/1993 | Wernicke et al. . |
| 5,292,344 | 3/1994 | Douglas . |
| 5,540,730 | 7/1996 | Terry, Jr. et al. .......................... 607/40 |
| 5,836,994 | 11/1998 | Bourgeois .................................. 607/40 |
| 5,861,014 | 1/1999 | Familoni .................................... 607/40 |

FOREIGN PATENT DOCUMENTS

| | | |
|---|---|---|
| 2 237 648 | 7/1973 | France . |
| 2 453 630 | 4/1979 | France . |
| 0571 938A2 | 5/1993 | Germany . |
| 1651918A1 | of 0000 | U.S.S.R. . |
| WO 94/27672 | 5/1994 | United Kingdom . |

*Primary Examiner*—Kennedy Schaetzle
*Attorney, Agent, or Firm*—Thomas F. Woods; Michael J. Jaro; Harold Patton

[57] ABSTRACT

Method and apparatus for providing on-demand stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensor for sensing abnormalities in gastric electrical activity. The pulse generator further features means for recognizing the type of gastric abnormality sensed. That is means for detecting whether gastric arrhythmia, bradygastria, dysrhythmia, tachygastria or retrograde propagation or uncoupling are present. If any of these gastric rhythm abnormalities are detected, then the pulse generator features means for emitting stimulation pulse trains to the gastric system to treat the detected gastric rhythm abnormalities. The stimulation pulse trains may take many forms and may be emitted for various periods of time.

11 Claims, 14 Drawing Sheets

| Abnormality | Processing/Detection | Decision-making Threshold |
|---|---|---|
| Arrhythmia | Zero crossing | Period>30 s |
| Bradygastria | Zero crossing | Period>30 s |
| Dysrhythmia | Zero crossing | $|(T_i - T_{i+1})/T_i| > 0.1$ |
| Retrograde propagation | Cross-correlation | $Phase_{distal} - Phase_{proximal} < 0$ |
| Tachygastria | Zero crossing | Period<16 s |
| Uncoupling | Cross-correlation | $T_{distal} \neq T_{proximal}$ |

APPARATUS FOR SENSING AND STIMULATING GASTROINTESTINAL TRACT ON-DEMAND

This is a Continuation-in-Part of Ser. No. 08/846,783 filed Apr. 30, 1997, now U.S. Pat. No. 5,861,014.

FIELD OF THE INVENTION

The invention relates to the field of smooth muscle disorders. In particular, the invention relates to treatment of gastrointestinal disorders using a method and apparatus for providing on-demand stimulation of the gastrointestinal tract.

BACKGROUND OF THE INVENTION

The gastrointestinal tract is responsible for an essential step in the digestive process, the reception of nutrition in the human body. Nutrition is received by absorbing mucosa in the gastrointestinal tract, using a very complex mechanism. An important element of the digestive process is intestinal peristalsis, the coordinated and self-regulated motor activity of the intestinal tract. Peristalsis is accomplished through a coordinated combination of electrical, chemical, and hormonal mediation, possibly in addition to other unknown mechanisms.

It is known that many diseases and maladies can affect the motor activity of the gastrointestinal tract, causing malfunction of the digestive process. Such diseases include diabetes mellitus, scleroderma, intestinal pseudo-obstruction, ileus, and gastroparesis. Other maladies such as tachygastria or bradygastria can also hinder coordinated muscular motor activity of the bowel.

Gastroparesis, for example, is a chronic gastric motility disorder in which there is delayed gastric emptying of solids plus or minus liquids. Symptoms of gastroparesis may range from early satiety and nausea in mild cases to chronic vomiting, dehydration, and nutritional compromise in severe cases. Diagnosis of gastroparesis is based on demonstration of delayed gastric emptying of a radio-labeled solid meal in the absence of mechanical obstruction. A number of gastrointestinal and systemic disorders may impair gastric motility with resultant gastroparesis. Approximately one third of patients with gastroparesis have no identifiable underlying cause (often called idiopathic gastroparesis). Management of gastroparesis involves four areas: (1) nutritional support, (2) antiemetic drugs, (3) prokinetic drugs, and (4) surgical therapy (in a very small subset of patients.) Gastroparesis is often a chronic, relapsing condition; 80% of patients require maintenance antiemetic and prokinetic therapy and 20% require long-term nutritional supplementation. In the near future, the most promising advances in the treatment of patients with gastroparesis will most likely come from the area of combination pharmacological therapy. In the long term, developments in the area of gastrointestinal pacing and transplantation may offer further treatment options in this difficult disorder.

The undesired effect of these conditions is a reduced ability or complete failure to efficiently propel gastrointestinal contents down the digestive tract. This results in malassimilation of liquid or food by the absorbing mucosa of the intestinal tract. If this condition is not corrected, malnutrition or even starvation may occur. Whereas some of these disease states can be corrected by medication or by simple surgery, in most cases treatment with drugs is not adequately effective, and surgery often has intolerable physiologic effects on the body.

It is known that motor activity can be recorded as electrical activity of the muscle. Traditionally, motor activity has been measured using recording electrodes placed directly on the muscle of the gastrointestinal tract, or on the skin external to the intestinal tract. For example, electrocardiograms measure the electrical activity of the heart in this manner.

Presently, however, there is no practically effective device or system to stimulate, record, or intelligently alter the muscular contractions of smooth muscle and the gastrointestinal tract in particular. Therefore, there is a need in the art for a system and method to properly pace gastrointestinal motor activity for correcting ineffective or absent propulsive electrical muscular activity of the gastrointestinal tract.

The muscle in the gastrointestinal tract differs from muscle elsewhere in two major ways. First, most of the muscle in the gastrointestinal tract is of the type called smooth muscle. There are several fundamental differences between the way smooth muscle and skeletal muscle function.

First, smooth muscle lacks a discrete end-plate (a defined region of interaction between the nerve ending and muscle, as seen in skeletal muscle); instead nerve fibers run from each axon parallel to the muscle bundle and end somewhat arbitrarily at various points along its length.

Secondly, unlike skeletal muscle, smooth muscle cells are coupled electrically within large bundles by means of connecting bridges. An electrical event at any region in the bundle is therefore conducted in a decremental fashion to other regions.

Thirdly, each muscle bundle receives input from multiple axons in the form of either excitatory or inhibitory signals. This is in contrast to skeletal muscle outside the gastrointestinal tract, where typically only one type of neurotransmitter is operative.

In addition, the gastrointestinal muscle is organized and regulated very differently than muscle elsewhere. Both skeletal and smooth muscle in the gastrointestinal tract are under the control of the enteric nervous system which is an extremely complex network of nerves and muscles, that resides within the gastrointestinal wall and orchestrates the entire digestive process including motility, secretion and absorption. The enteric nerves are also organized into interconnected networks called plexuses. Of these, the myenteric plexus, situated between the circular and longitudinal muscle layers, is the main modulator of gastrointestinal motility. It receives input from both the central nervous system (via vagal and sympathetic pathways) as well as from local reflex pathways. Its output consists of both inhibitory and excitatory signals to the adjacent muscle.

The final neural pathway regulating muscle activity in the gastrointestinal tract is therefore represented by the neurons of the myenteric plexus. A useful, if somewhat simplistic concept is to visualize net muscle tone in the gastrointestinal tract as that resulting from the balance between the opposing effects of two neuronal systems in the myenteric plexus: one causing the muscle to contract (mainly via acetylcholine) and the other causing it to relax. Both types of neurons, however, are activated by acetylcholine within the myenteric plexus. The role of acetylcholine in the regulation of gastrointestinal muscle tone is therefore complex. Acetylcholine directly released by effector nerves near the muscle causes contraction; however, within the myenteric plexus, it may result in inhibition or excitation. This is in contrast to skeletal muscle outside the gastrointestinal tract which is directly innervated by nerves emanating from the central nervous system. The interaction between nerve and muscle in skeletal muscle outside the gastrointestinal tract is far more simple: nerves release acetylcholine which causes the muscle to contract.

Finally, the myenteric plexus is probably the most important but not the only determinant of muscle tone in the gastrointestinal tract. In fact, basal smooth muscle tone may be visualized as resulting from the sum of many different factors including intrinsic (myogenic) tone, and circulating hormones, in addition to nerve activity.

It should be clear therefore, that the regulation of gastrointestinal tract muscle motility is far more complex than that of skeletal muscle outside the gastrointestinal tract.

There is a need in the medical arts for methods and devices for treatment of gastrointestinal disorders including achalasia, other disorders of the lower esophageal sphincter, sphincter of Oddi dysfunction, irritable bowel syndrome, etc., which treatments will be long-lasting and devoid of significant rates of complication.

SUMMARY OF THE INVENTION

It is an object of the invention to provide methods for in vivo treatment of mammals with dysfunctional gastrointestinal muscle or disorders of smooth muscles elsewhere in the body.

It is another object of the invention to provide a device for in vivo treatment of mammals with dysfunctional gastrointestinal muscle or smooth muscles elsewhere in the body.

These and other objects are provided by one or more of the embodiments described below the present invention is a method and apparatus for providing on-demand stimulation of the gastrointestinal tract. The apparatus features an implantable pulse generator which may be coupled to the gastric system through one or more medical electrical leads. In the preferred embodiment the leads couple to the circular layer of the stomach. The pulse generator preferably features sensor for sensing abnormalities in gastric electrical activity. The pulse generator further features means for recognizing the type of gastric abnormality sensed. That is means for detecting whether gastric arrhythmia, bradygastria, dysrhythmia, tachygastria or retrograde propagation or uncoupling are present. If any of these gastric rhythm abnormalities are detected, then the pulse generator features means for emitting stimulation pulse trains to the gastric system to treat the detected gastric rhythm abnormalities. The stimulation pulse trains may take many forms and may be emitted for various periods of time.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein.

The FIGS. are not necessarily to scale.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims. Moreover, although the device is particularly illustrated to treat the stomach, this is done only for purposes of illustration. The present invention may be used to treat any of the various organs and associated conditions of the gastrointestinal tract, including the large and small bowel, as well as the esophagus.

Figure 1:
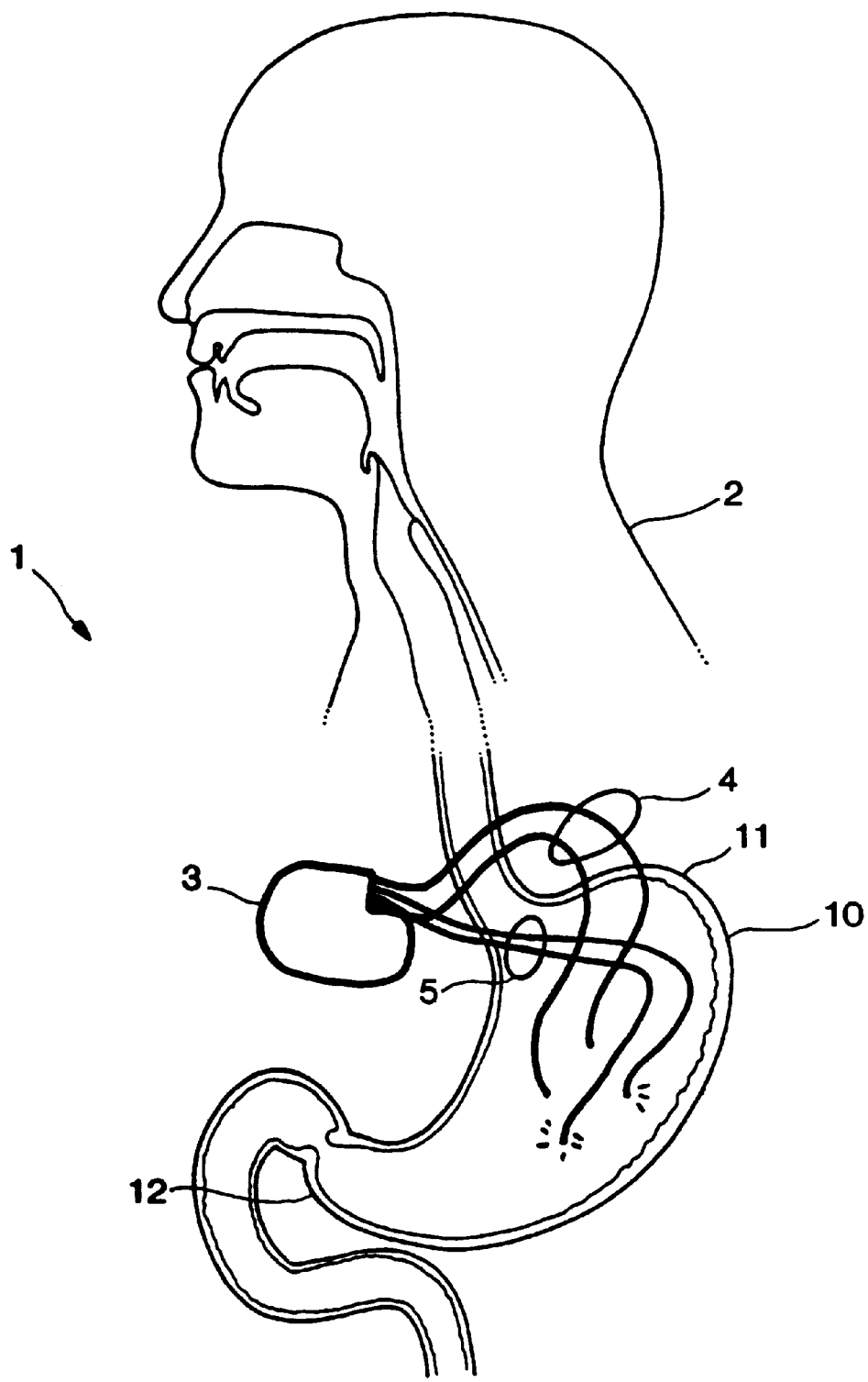
FIG. 1 depicts the apparatus implanted within a patient.

FIG. 1 shows a system 1 implanted in a patient 2. As seen, the system 1 comprises an implantable pulse generator 3 featuring two sets of leads 4, 5 which are coupled to the stomach 10. The first set of leads 4 provide stimulation to the stomach. The second set of leads 5 provide sensing of the gastro electrical activity of the stomach 10 to the pulse generator 3. In the preferred embodiment, the pulse generator 3 is implanted within the patient 2, and thus is hermeticly enclosed, as is well known in the art. The leads used for both the first set 4 and the second set 5 may be any acceptable lead. In the preferred embodiment, the preferred leads are Medtronic Model No. 4300 intramuscular lead. Of course, other configurations of leads or lead systems may be used, including other leads designs as well as more or less sets of leads.

The first set of leads 4 are stimulation leads which conduct stimulation pulses from the pulse generator 3 to the stomach 10. First set of leads 4 are preferably implanted at the junction of the corpus and antrum of the stomach 10 in essentially a line along the greater curvature running from the fundus 11 to the terminal antrum 12. Of course, other locations for first set of leads 4 may be used, such as in the caudud corpus as well as the orad or terminal antrum. The second set of leads 5 are sensing leads which conduct any gastroelectrical activities sensed in the stomach 10 to the pulse generator 3. Preferably the second set of leads 5 are positioned in close proximity to the stimulating electrode, about 2 cm. from the pacing or first set of leads 4 in the direction of the antrum 12. Of course the functions of stimulating and sensing may be equally performed by both sets of leads, i.e. each set of leads may be used to both sense and stimulate the tissues.

Figure 2:
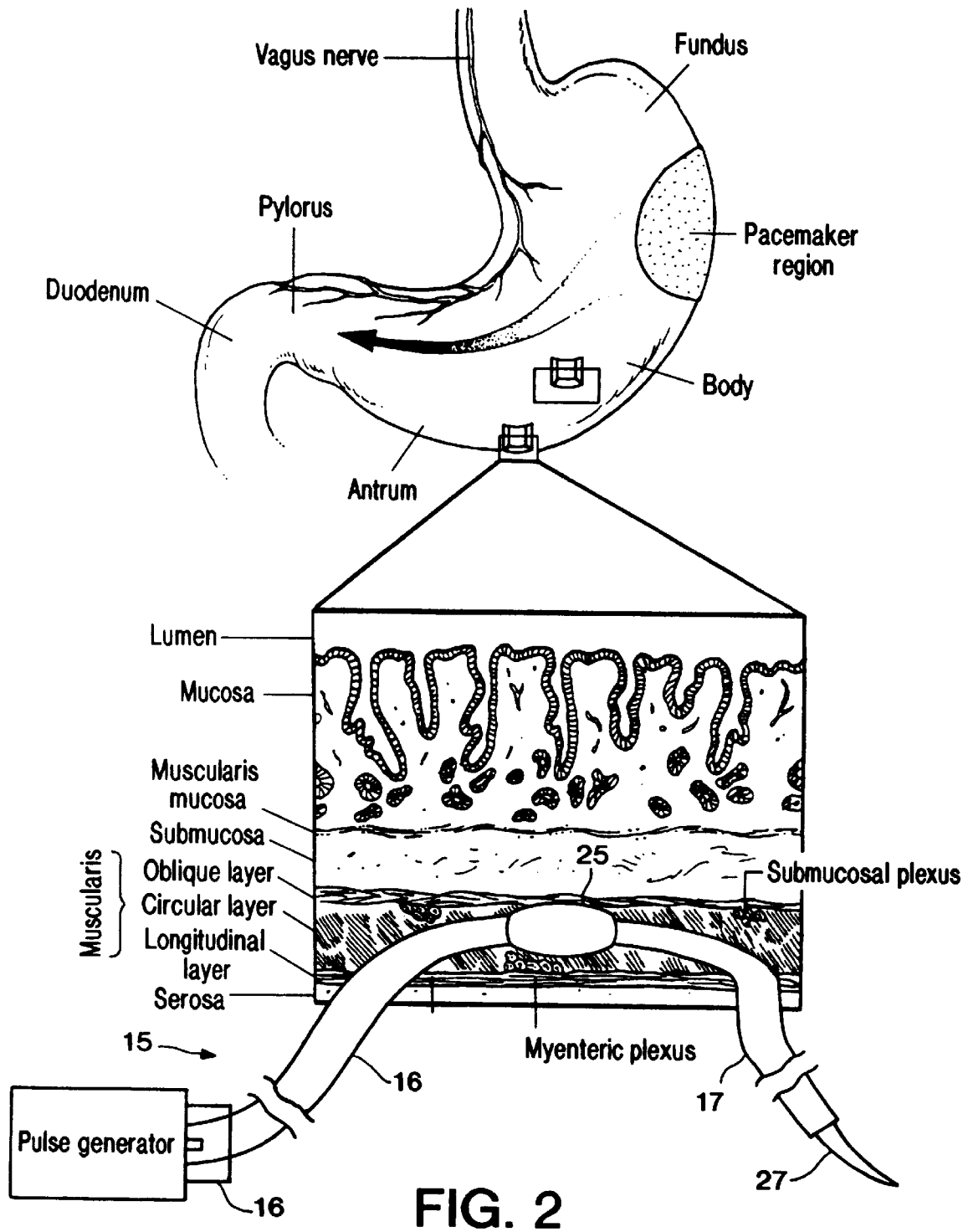
FIG. 2 depicts a detailed view of the stomach muscle showing the electrode of the lead implanted.

FIG. 2 details the preferred positioning of an electrode of a lead within the various layers of the stomach. As seen, the stomach 10 has essentially seven layers of tissue. In the preferred embodiment, the electrode of each lead is positioned into the layers of the stomach muscle as shown. That is, the electrode is positioned such that it intersects both the longitudinal and circular layers. This is believed important by the inventor because in such a manner the electrode is able to also intersect the integral nerve fibers of the stomach, carried with the cells of Cajal. Of course, other types of electrodes or lead systems may be used, including those which contact only any one of each of the layers of the stomach organ, such as only the mucosa or only the serosa. Moreover, although in the preferred embodiment a pair of unipolar leads are used for stimulation and a second pair of unipolar leads are used for stimulation, other configurations of leads may be used, such as bipolar, tripolar, quadrapolar, as well as any other suitable configuration.

Figure 3:
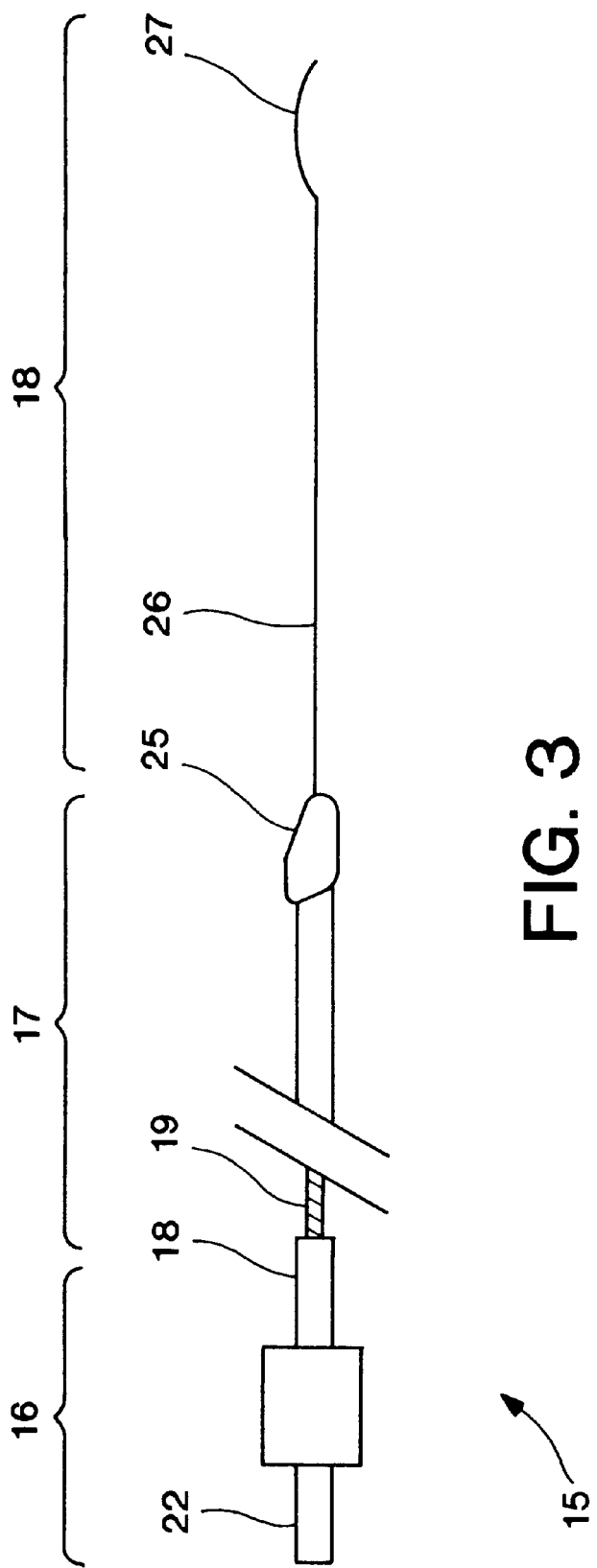
FIG. 3 depicts a plan view of a lead used with the apparatus.

FIG. 3 depicts a plan view of the preferred embodiment lead 15 used in the present invention. As seen, the lead 15 essentially has three sections, connector section 16, body section 17 and fixation section 18. Connector section 16 includes a connector pin 22 to electrically couple the lead 15 into the pulse generator. Any connector pin 22 as well known in the art may be used. Body section 17 includes an electrical conductor 19 surrounded by an electrical insulator 20. In the preferred embodiment electrical conductor 19 is a platinum iridium alloy and electrical insulator 18 is silicone. Of course, other biocompatible materials may also be used. As seen, at the distal end of the body section 17 is an electrode 25. In the preferred embodiment, electrode 25 is a polished platinum iridium alloy. Of course, other materials may likewise be used, such as a porous platinized structure. In addition, the electrode 25 could further feature various pharmaceutical agents, such as dexamethasone sodium phosphate or beclomethasone phosphate in order to minimize the inflammatory response of the tissue to the implanted lead 15. Located distal to the electrode 25 is the fixation section 18. As seen, fixation section 18 has essentially two piece parts, a suture 26 which is in turn coupled to a needle 27. Suture 26 includes a fixation coil 28 along its length. Needle 27 is preferably curved. As is well known in the art, fixation coil 28 cooperates with the body tissue after implantation to maintain the lead 15 in the position implanted. Of course, other fixation mechanisms may be used, such as fixation discs, as is well known in the art.

Figure 4:
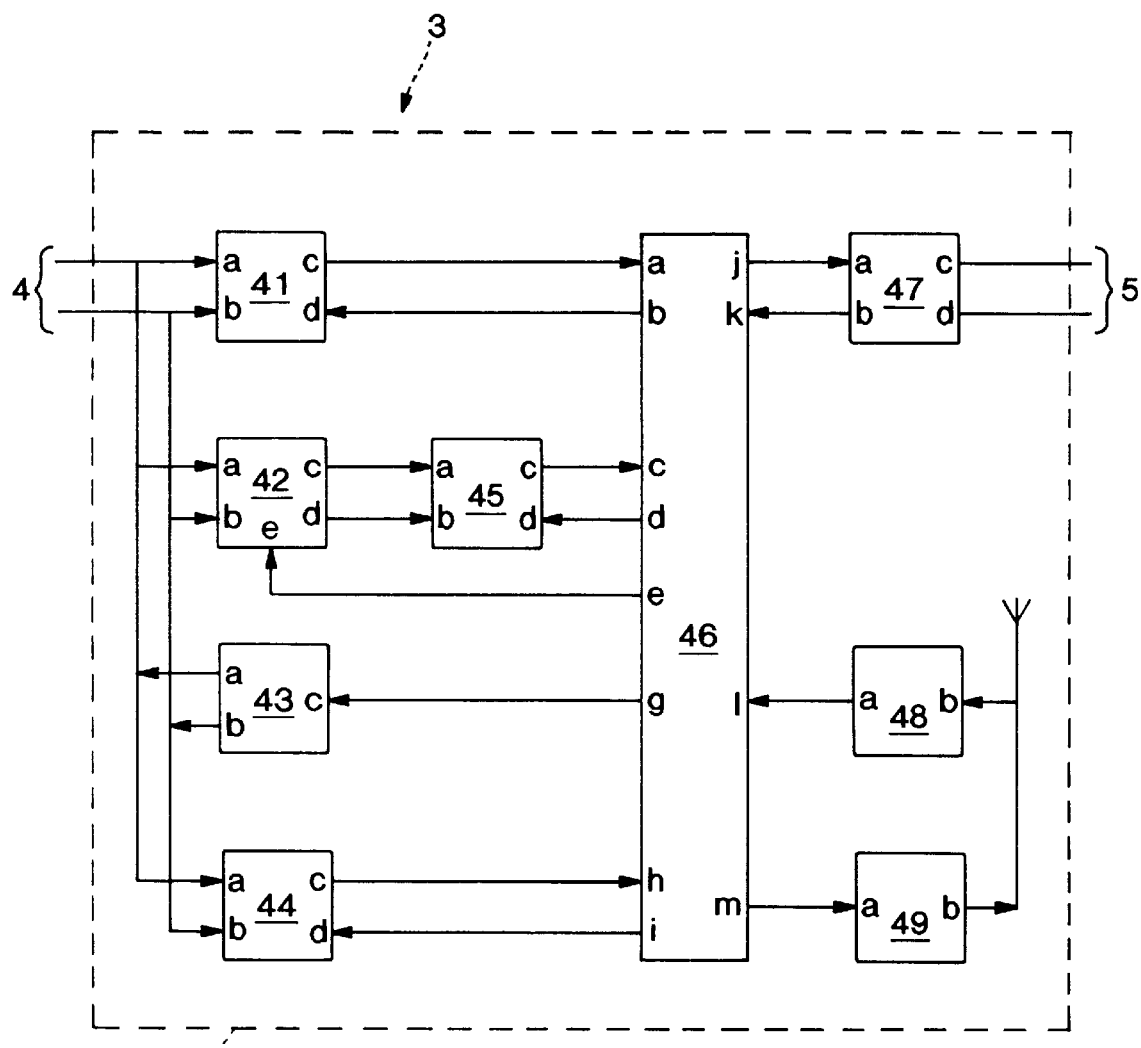
FIG. 4 is a functional block diagram of the pulse generator.

FIG. 4 depicts a functional block diagram of the gastrointestinal pulse generator according to the present invention. As seen, pulse generator 3 is enclosed by hermetic enclosure 40 to protect pulse generator 3 when implanted. Hermetic enclosure may consist of any suitable construction. Pulse generator 3 couples with two sets of leads 4, 5 which are, in turn, coupled to the stomach 10. The first set of leads 4 transmits stimulation pulses from pulse generator 3 to the stomach. The second set of leads 5 provide sensing of the gastro electrical activity of the stomach 10 to the pulse generator 3. Although in the preferred embodiment the stimulating leads and sensing leads are separate leads, the present invention may also be employed using a combination of lead which both sense and stimulate.

As seen, the sensing leads 4 are coupled into a slow wave detection circuit 41. Slow wave detection circuit 41 includes a band pass amplifier, a slew rate converter and two threshold detectors. Essentially, such a slow wave detection circuit 41 is similar to those used in a cardiac pacemaker but with several important characteristics. First, the band pass amplifier has a much lower center frequency, preferably on the order of 0.3 Hz (18 bpm). The slew rate converter generates a signal corresponding to the sensed slew rate of the sensed signal. The output of the slew rate detector, as is well known in the art, is directly related to the sensed slew rate of the sensed signal. The threshold detectors generate output signals when the sensed input signal is above a threshold level. One threshold detector corresponds through the band pass amplifier to the peak to peak amplitude of the sensed electrogastrogram. The second threshold detector corresponds to the sensed slew rate.

Preferably, the slow wave detection circuit 41 must be able to detect input signals between 30 microvolts and 10 millivolts which have a slew rate between 100 microvolts per/second up to 10 millivolts per/second with a typical value of 1 millivolt per second. Such a range may be achieved using multiple steps which are controlled by the microprocessor 46 via the input line 46*b*–41*d*. To detect the slow wave, both threshold detectors should be coupled using a logical OR configuration. Thus, a signal should then be sent via the output line 41*c*–46*a* to the microprocessor 46. The slew rate detector may also include an interference detector specially designed to detect power field variations as is well known in the pacing art.

The band pass amplifier should be blanked for a period after a sensed event has been received by the microprocessor 46 or just before stimulation pulse is emitted by output stage discussed below. The microprocessor 46 should also ignore sensed output signals during a period after a sensed or paced event. This is similar to a blanking circuit where sensed events during a blanking period do not affect the timing of the pulse generator. In the preferred embodiment, the blanking period is on the order of between 0.5 to 3.0 seconds. After the blanking period, during a certain timing window, the microprocessor 46 may receive slow wave detection signals, which will not restart the pulse generator timing circuit, but will instead be interpreted as interference by the microprocessor 46. This timing window, interference detection timing window, may be up to seven seconds in duration after the sensed or paced event.

As seen, blanking switch 42 is coupled to sensing electrodes 4 as well as to amplifier 45. The operation of blanking switch 42 causes the amplifier 45 to be connected to the sensing electrodes 4 once an intrinsic deflection has been detected or a stimulus has been emitted. Preferably, this occurs after a short delay. Blanking switch 42 is closed between 1 to 2 seconds after the events and opens roughly 5 to 7 seconds later or at approximately 30% of the intrinsic event interval. As seen, the switch is controlled via the line 6*e*–2*e*.

Also coupled to the sensing electrodes 4 is an AC current generator 43. This AC current generator 43 is part of a plethysmorgraphy circuit. Overall, the plethysmorgraphy circuit is comprised from AC current generator 43, amplifier, modulator and ADC converter 44 as well as a portion of the microprocessor 46. The AC current generator 43 is switched on via signal from microprocessor 46 once a slow wave is detected or a pacing stimulus is emitted. It is switched off roughly 10 seconds after being switched on also from the same line or signal from the microprocessor 46. The AC current generator 43 amplitude and frequency are programmable via microprocessor 46. The frequency should be such it is not detected by amplifier 4. If synchronous detection by amplifier 4 occurs at the end of the blanking period, then the amplitude and/or the frequency of the AC current generator 43 is adjusted by the microprocessor 46 to avoid subsequent detection of the generated AC current. Overall, the plethysmorgraphy circuit is present to provide a means for sensing mechanical activity of the underlying tissue. That is, whereas the electrogastrogram may be sensed using electrical pickups, the contraction of the gastrointestinal tract may be sensed using the plethysmorgraphy circuit.

Turning now to the amplifier, the modulator and ADC converter 44, the AC voltage caused by the injection of AC current generator 43 is amplified and demodulated and converted in order to detect impedance changes caused by contractions of the underlying tissue. The ADC converter digitizes the amplitude of the demodulated signal. The digitized signal is transmitted via line 44c–46h to the microprocessor 46. The microprocessor 46 analyzes the signal pattern by comparing it with one or more templates to identify it as a contraction as well as to reject interference or signals generated by postural changes or vomiting. This template comparison is done synchronously with the detection of the slow wave. Line 46i–44d is used to control the amplifier and ADC from the microprocessor 46.

The microprocessor 46 handles all timings and data storage of the pulse generator and may be of any suitable design. The description of the microprocessor 46 function is described in the section below which details the operation of the algorithm used in the present invention.

Stimulation pulses are generated by the output stage 47. In the preferred embodiment, the output stage 47 generates pulse trains consisting of 2 pulses of 300 microseconds duration each spaced apart by one second, where each pulse train, in turn is further spaced apart by 4 seconds. Of course, many other pulse trains may also be delivered, including constant current or constant voltage outputs, or a mixture of both. The output pulses are transported to the gastrointestinal tissue via medical electrical leads 5 and thus to the stomach.

Turning again to the output stage 47, when an output pulse is to be delivered, its amplitude, pulse width and duration and frequencies are controlled via lines 46j–47a. If it is a burst of stimuli, the frequency and duration are controlled through the same line while a burst finished signal is sent to the microprocessor 46 via output line 47b–46k.

Programmability to the pulse generator 3 is achieved through receiver-demodulator 48 and transmitter 49. As seen, each of these devices is coupled to the microprocessor 46. The receiver-demodulator 48 and transmitter 49 are similar to those used in cardiac pacemakers.

Figures 5, 6:
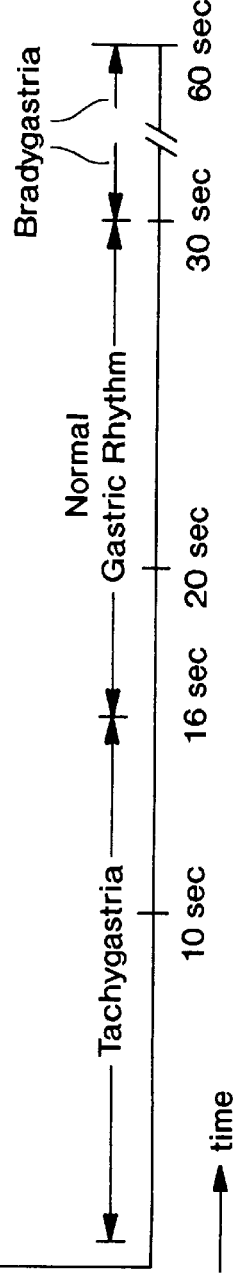
FIG. 5 is a table listing the gastric arrhythmias or abnormalities which may be detected and treated using the present invention.
FIG. 6 which illustrates the detection interval ranges which may be employed in a preferred embodiment of the present invention.

FIG. 5 is a table listing the gastric arrhythmias or abnormalities which may be detected and treated using the present invention. In the preferred embodiment, the gastric arrhythmias or abnormalities are processed or detected using either a zero-crossing analysis or cross-correlation or both. As seen, in the present invention, the detection of an arrhythmia is used with a zero-crossing analysis. The decision making threshold is the period between gastric slow waves is greater than 30 seconds. Of course, other values may be used. Bradygastria is defined on a similar basis as an arrhythmia. If a stable period greater than 30 seconds is sensed, then a bradygastria is detected. Dysrhythmia is detected if irregular periods of the EGG exhibits cyclic activities having variations of more than 10% in the period of successive cycles of the activity. As seen, this is determined using the simple mathematical formula of averaging the periods between two sensed slow waves and whether or not the period variation is greater than 0.1 which corresponds to 10%. Mathematically, this is expressed as $(T_i-T_{i+1})/T_i|>0.1$ Tachygastria is detected also using zero-crossing analysis and is detected if a stable signal of the successive period of less than 16 seconds is detected. Two other types of abnormalities are also detected using the present invention using a zero-crossing analysis. As seen, the retrograde propagation is detected by examining the relative phase angle between two signals. If the more distal signal sensed is in advance of or leads the proximal signal sensed, then retrograde propagation is detected. Uncoupling is also detected using cross-correlation techniques. As seen, uncoupling is detected by comparing the two channels, and if they exhibit dissimilar periods between the two slow waves then uncoupling is detected.

Turning now to FIG. 6 which illustrates the detection interval ranges which may be employed in a preferred embodiment of the present invention. The specific interval ranges are selected and programmable by the physician. As seen, events which occur less than one second apart are not detected due to blanking. This is a fixed interval and its length is not programmable by the physician. The range of intervals between detected events taken as indicative of tachygastria are greater than 1 second and less than 16 seconds. That is, the tachygastria detection interval extends to 16 seconds. This range is programmed and is selected by the physician to suit the particular patient and the lead configuration used. The lead of intervals between detected events taken as indicative of normal gastric rhythm are greater than 16 seconds and less than 30 seconds. That is, the normal gastric rhythm detection interval extends to 30 seconds. This range is also programmed and is selected by the physician to suit the particular patient and leads used. Events having intervals which occur after 30 seconds up to 60 seconds, in the preferred embodiment, are taken as indicative of bradygastria. That is, the bradygastria escape interval extends up to 60 seconds. This range is also programmed and is selected by the physician. Events which occur at intervals greater than the bradygastria escape interval would not be detected as the bradygastria escape interval would time out at 60 seconds and the device would recycle and deliver a therapy. Examples of how these detection intervals function are as follows. If a first event is sensed and a second event is sensed 10 seconds later, then a tachygastria is provisionally detected. If a first event is sensed and a second event is sensed 40 seconds later, then a bradygastria is provisionally detected. As a third example, if a first event is sensed and a second event occurs less than one second later and a third event occurs 20 seconds after the first event, then a normal gastric rhythm is sensed. This is so because the second event occurred during the blanking period and thus was not sensed (the third event was thereafter sensed a sum of 20 seconds after the first event, well within the normal gastric rhythm interval range).

It should be noted that these specific times for the intervals is for the preferred embodiment and thus is only illustrative of the present invention. Other interval ranges may also be used within the scope of the present invention.

Figure 7:
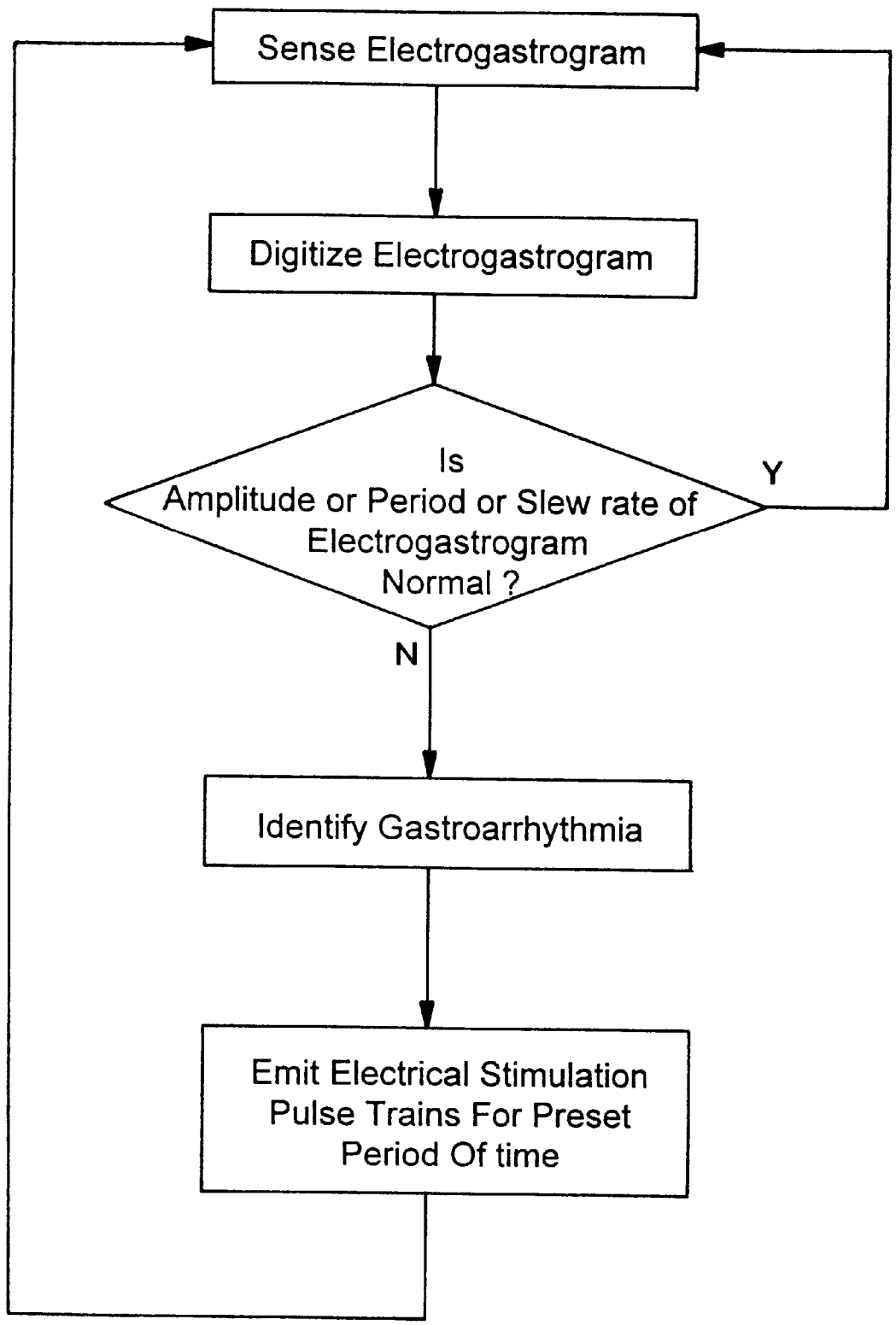
FIG. 7 is a functional block diagram illustrating the present invention.

FIG. 7 is a functional block diagram illustrating the present invention. As seen, the present invention senses as, a first step, the electrogastrogram. This is accomplished using the sensing leads board depicted in FIG. 1. Next, the electrogastrogram is digitized using the microprocessor. Next, the amplitude, period and slew rate of the electrogastrogram are analyzed. If either the amplitude or period or slew rate of the electrogastrogram are abnormal, then the device drops down to identify the gastroarrhythmia detected. Such identification of the gastroarrhythmia is done using the criteria set forth in FIG. 5, discussed above. Once an accurate diagnosis has been reached using the criteria set forth in FIG. 5, then the device proceeds to emit electrical stimulation pulse trains for a preset period of time. If, however, the amplitude and period and slew rate of the electrogastrogram are normal, then the device resets itself and proceeds back to sense the electrogastrogram.

Figure 8:
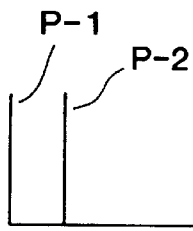
FIG. 8 details the preferred stimulation pulse train emitted.

FIG. 8 details the preferred stimulation pulse train emitted. As seen, the preferred pulse train consists of two pulses P-1 and P-2 of 300 microseconds duration each spaced apart by 1 second, where each pulse train, in turn, is further spaced apart from one another by 4 seconds, as illustrated. Of course, many other pulse trains and timing schemes may also be delivered, including constant current or constant voltage outputs, or a mixture of both. The output pulses are transported to the gastrointestinal tissue via medical electrical leads 5 and thus to stomach.

Figure 9:
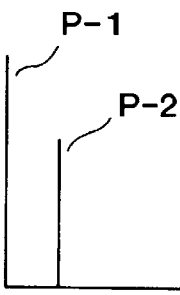
FIGS. 9–11 details the alternate stimulation pulse trains which may be emitted.

FIG. 9 details an alternative embodiment of pulse trains delivered for a preset period of time to the stomach. As seen, in this alternative embodiment, pulse trains P-1 and P-2 are delivered which have a decreasing amplitude.

Figure 10:
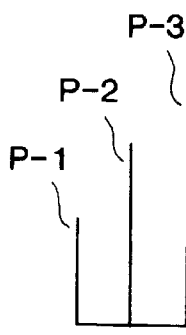
Figure 11:
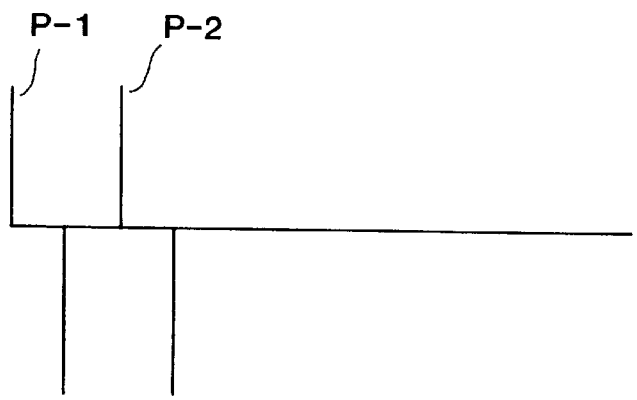

FIG. 10 and FIG. 11 further detail alternative embodiments for pulse trains used to stimulate the stomach for a preset period of time. As seen in FIG. 10 a pulse train having pulses P-1, P-2 and P-3 of increasing amplitude is delivered. In FIG. 11 a biphasic pulse train of pulses P-1 and P-2 is delivered.

Figure 12:
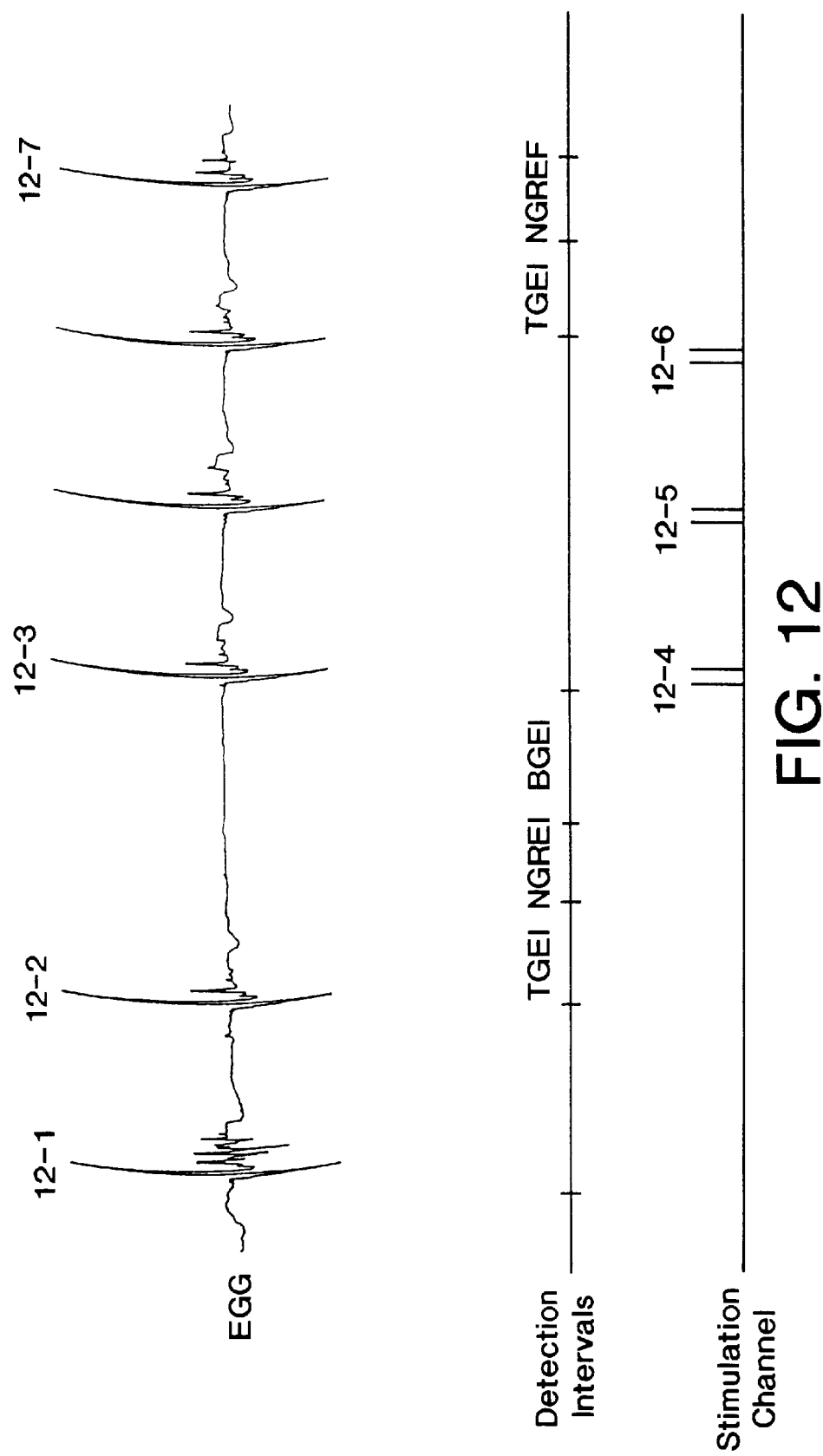
FIG. 12 depicts an exemplary EGG as detected by the present invention and the emitted stimulation to treat a detected arrhythmia.

FIG. 12 depicts an exemplary EGG as detected by the present invention and the emitted stimulation to treat a detected arrhythmia. As seen, the EGG typically exhibits periodic slow waves of approximately 25 seconds apart. As seen, slow wave 12-1 is followed by 12-2. Following the slow wave 12-2, another slow wave does not occur. As seen, the detection intervals are retriggered after each detected slow wave. In the example, the detection intervals which begin timing after slow wave 12-2 time out through the Tachygastria escape interval (TGEI) through the normal gastric rhythm escape interval (NGREI) and complete timing out through the end of the bradygastria escape interval (BGEI)I. Once the bradygastria escape interval (BGEI) is reached, the stimulation channel is activated in a series of pulse trains 12-4, 12-5 and 12-6 are initiated. These pulse trains are emitted for preset periods of time, in the examples shown for a period of 90 seconds. Once the preset period of time times out, the device again recycles to sense the EGG and detect whether or not a gastroarrhyhthmia is present. As seen, because slow wave 12-7 is sensed within the normal gastroarrrhythmia escape interval, no further electrical stimulation pulse trains are emitted.

Figure 13:
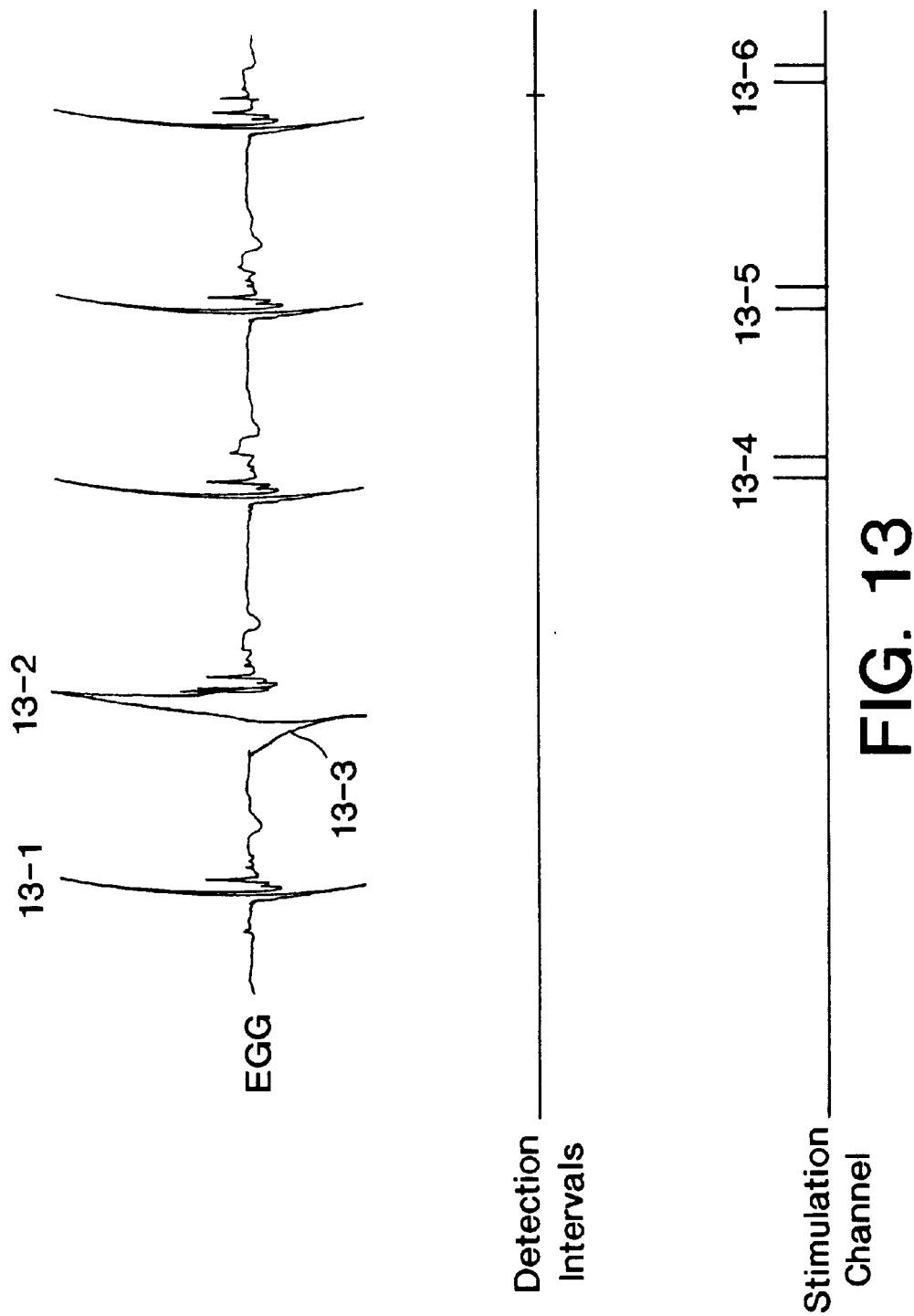
FIG. 13, this depicts a gastroarrhythmia which is detected due to the fact that the slew rate of the electrogastrogram is not normal.

Turning now to FIG. 13, this depicts a gastroarrhythmia which is detected due to the fact that the slew rate of the electrogastrogram is not normal. As seen, slow wave 13-1 is followed by slow wave 13-2. Slow wave 13-2, however, has an additional slew rate or slope of incoming excursion signal 13-3 less abrupt than that shown in 13-1. Due to this fact, the device then drops down and identifies the gastroarrhythmia. In response to the identified gastroarrhythmia, the device emits electrical stimulation pulse trains 13-4, 13-5 and 13-6 for a preset period of time to treat the detected arrhythmia.

Figure 14:
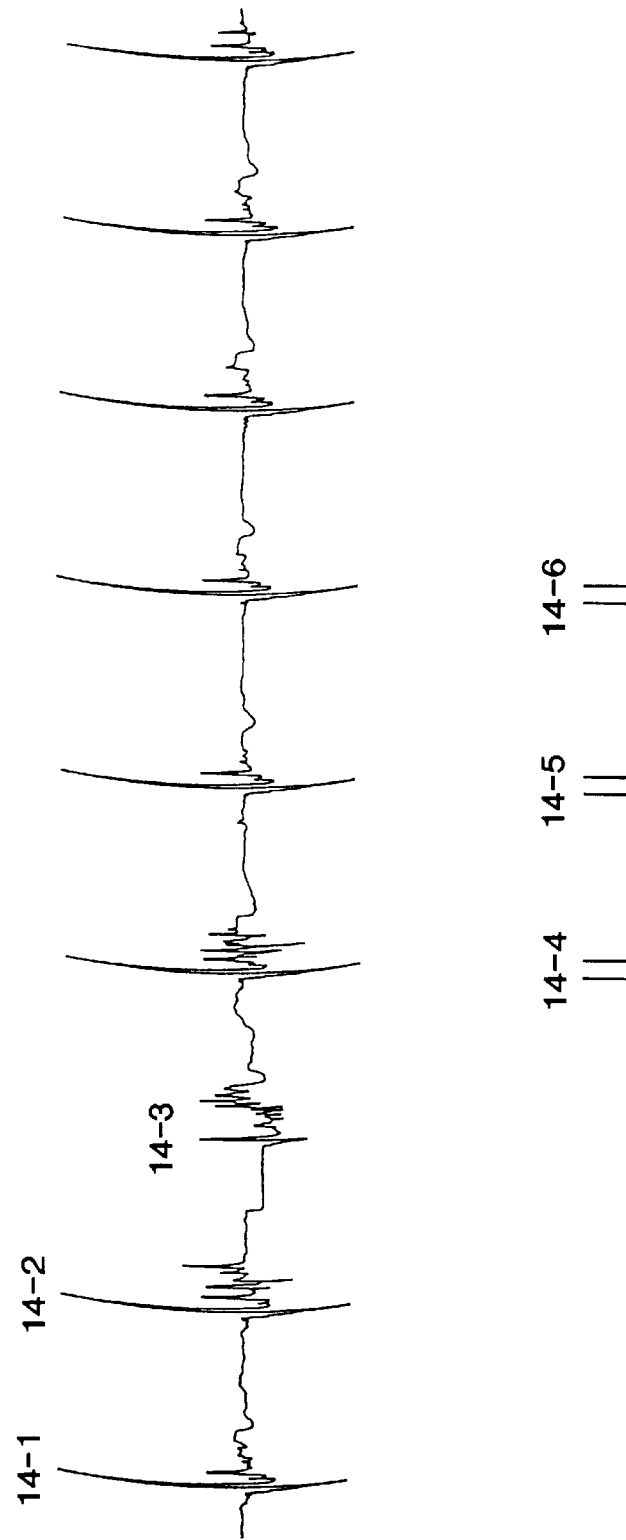
FIG. 14 depicts a further gastric arrhythmia which is detected due to the fact that is has a much lower amplitude.

FIG. 14 depicts a further gastric arrhythmia detected. As seen, slow waves 14-1, 14-2 are followed by a slow wave 14-3, having a much lower amplitude. As seen, in response to this sensed lower amplitude, the device emits electrical stimulation pulse trains for a preset period of time 14-4, 14-5, and 14-6.

Figure 15:
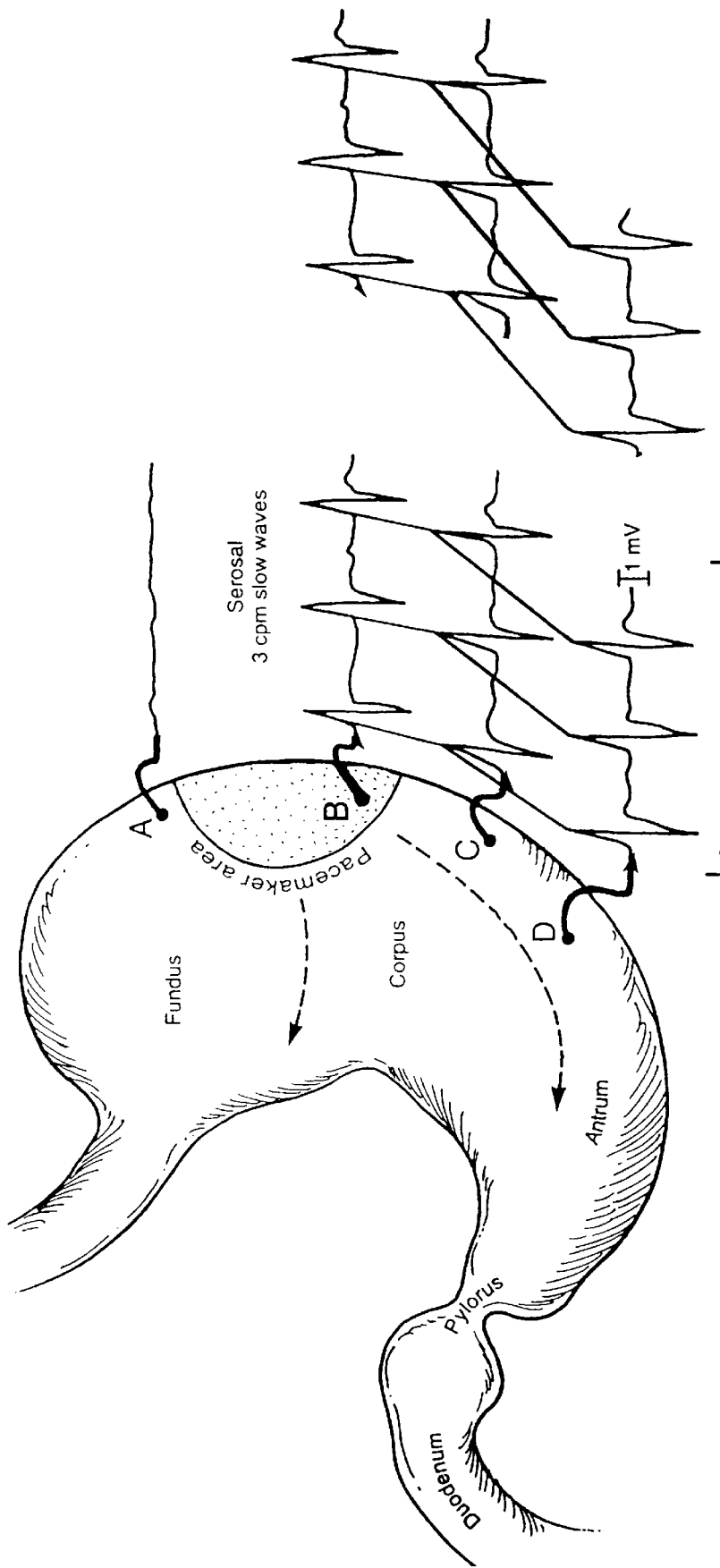
FIG. 15 depicts an example of a gastroarrhythmia which is detected by the present invention using cross-correlation.

FIG. 15 depicts an example of a gastroarrhythmia which is detected by the present invention using cross-correlation. As seen, slow waves typically begin in the pacemaker area located in the proximal gastric body along the greater curve as shown by the gray area. As discussed above, these slow waves spread circumferentially and distally and migrate through the antrum. These slow waves would be sensed by sensing electrodes C and D. The slow wave amplitude is higher and the propagation loss is faster in the distal antrum compared with the corpus. As seen, the slow wave dissolves in the terminal antrum while another slow wave begins to migrate distally again from the pacemaker region. Thus, as shown, three slow waves will propagate from proximal to distal stomach every 60 seconds. On occasion, the slow waves may become uncoupled or out of phase with one another. This is taken as an indicative of a gastroarrhythmia and would elicit an electrical stimulation for a preset period of time by the present invention. In this particular example, these slow waves have a greater period between one another than those otherwise normally seen. The effect of this uncoupling is that the slow waves depict retrograde propagation. That is the proximal sites are coupled to but lag in time relative to the distal sites. This is an abnormality detectable using a cross correlation technique, typically programmed into the microprocessor.

Figure 16:
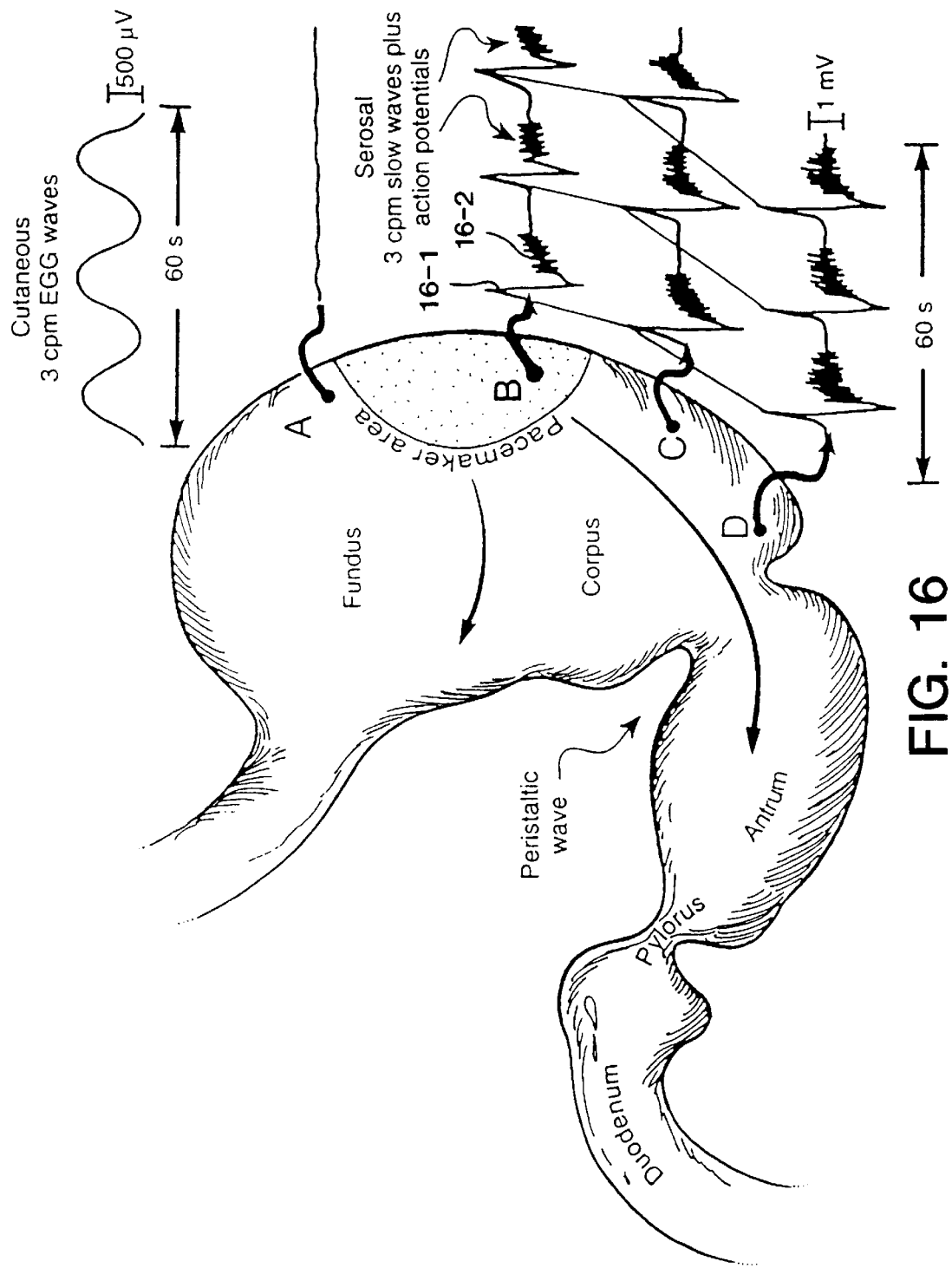
FIG. 16 depicts an example of a gastro rhythm which is detected by the present invention using a series of frequency selective sensors.

FIG. 16 depicts an example of a gastro rhythm which is detected by the present invention using separate frequency sensors. In particular FIG. 16 depicts the stomach undergoing a peristaltic contraction and the corresponding electrogastrogram along the same portions of the stomach. As seen, the peristaltic wave moves through the stomach towards the pyloric antrum. The peristaltic contraction functions to both force contents of the stomach into the duodenum as well as to create shear on the stomach contents and thus break the contents down into smaller particles. During a peristaltic contraction, the stomach continues to undergo slow waves 16-1. As seen, these slow waves typically occur at a rate of 3 per minute. During a peristaltic contraction, however, the slow waves further feature a high frequency action potential. As seen, each slow wave features a corresponding high frequency action potential 16-2 shortly thereafter. The slow waves, as discussed above, typically have a frequency of 3 per minute. The higher frequency action potentials, however, typically have a frequency of between 100–300 hertz. Thus a further embodiment of the present invention is directed to sensing both the slow waves and the higher frequency fast waves which follow and processing the sensed waves to indicate the state of the stomach at that moment. This is especially useful to thereby determine or detect the presence or absence of peristaltic contraction within the stomach or any other smooth muscle organ of the body.

Figure 17:
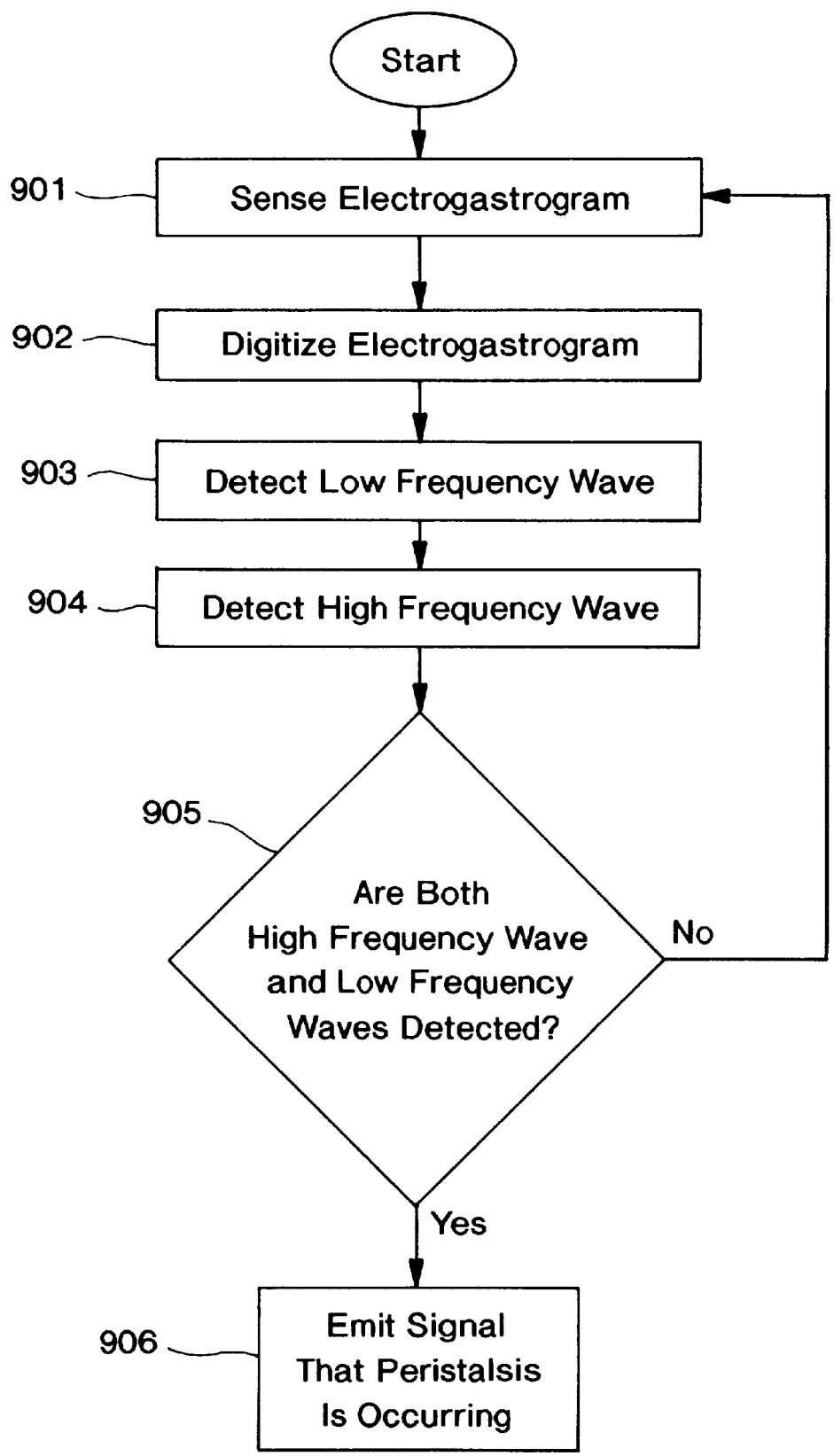
FIG. 17 is a flow diagram of a device used to detect the rhythm shown in FIG. 16.

FIG. 17 depicts the steps used to sense the rhythm shown in FIG. 16. As seen, at the first step 901, the electrogastrogram is sensed. Next, at 902 the electrogastrogram is digitized using the microprocessor. Next, the digitized data is analyzed for both a low frequency wave 903 and whether an higher frequency wave follows 904. If both a low frequency wave is detected which is followed by a high frequency wave 905, then the device drops down to signal peristalsis is occurring 906. If, however, only a low frequency wave or only a high frequency wave is detected, then the device resets itself and proceeds back to sense the electrogastrogram at step 901.

Figure 18:
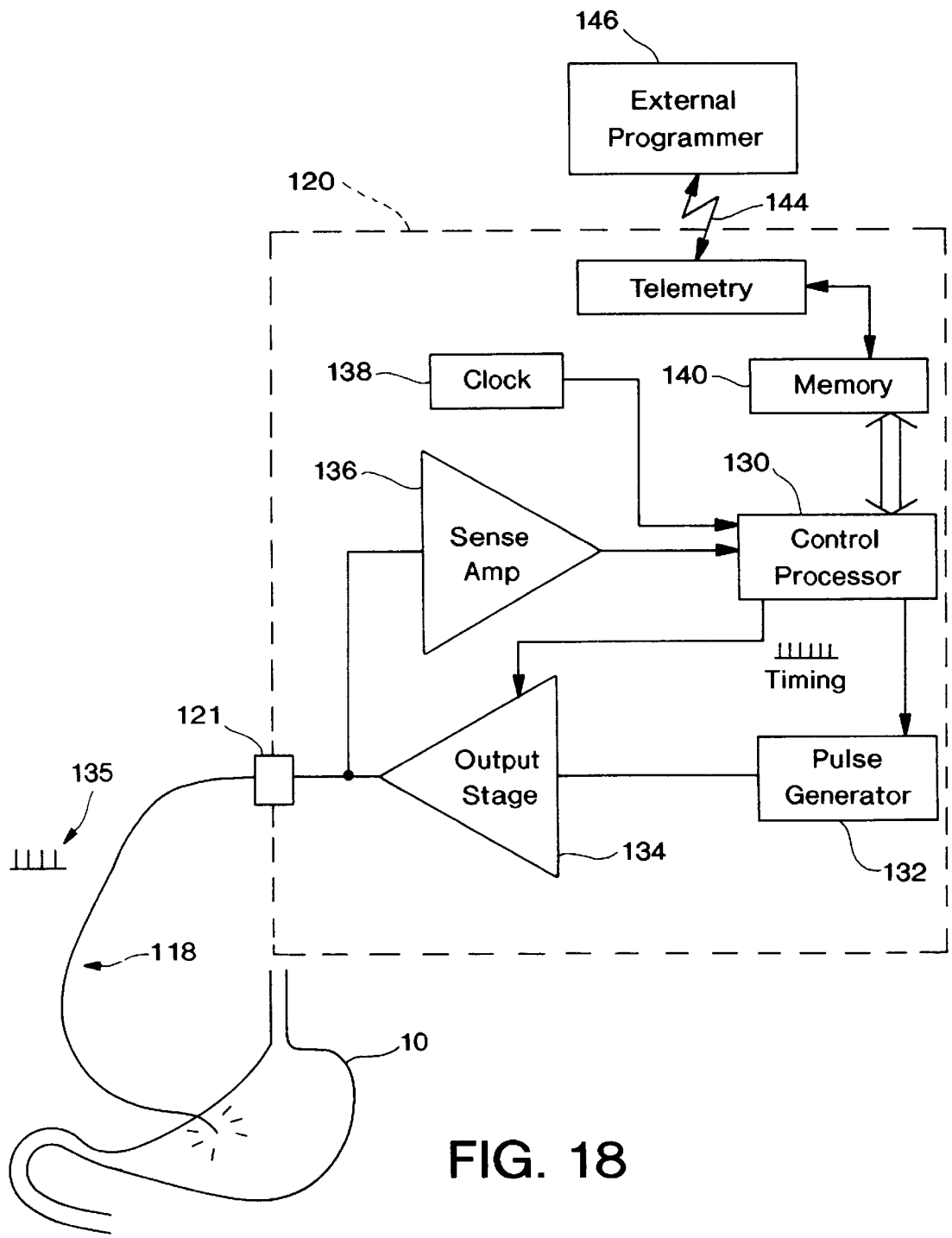
FIG. 18 shows a block diagram of an alternate embodiment of the present invention.

FIG. 18 shows a block diagram of an alternate embodiment of the present invention. That is in this alternate embodiment, the present invention may be practiced completely in the context of a software based system. As seen In this embodiment system 118 includes an implantable stimulator 120 which is used in conduction with an external programmer 146. Stimulator 120 includes an output connector 121 through which one or more medical electrical leads 124 may be connected to internal circuits of stimulator. In this embodiment lead is also typically Medtronic model 4300 intramuscular lead. Although a single lead 124 is shown used to couple stimulator 20 to gastrointestinal tract, it is to be understood use of a single lead in this manner is only exemplary, as the invention may be used equally well with systems that include multiple leads that make contact with multiple locations within gastrointestinal tract or other body tissue locations.

Included within internal circuits of stimulator with which lead 124 makes contact when inserted into connector 121 include an output amplifier 134 and a sense amplifier 136. Output amplifier 134 generates an electrical stimulation pulses 135 as controlled by a pulse generator 132. Pulse generator 132, in turn, receives timing signals from a control processor 130. Such timing signals control when stimulation pulses 135 are to be generated. Sense amplifier 136 monitors electrical signals appearing on lead 124, and processes such signals.

Processing typically includes amplification, filtering, and threshold detection. If a valid depolarization signal ("intrinsic event") is sensed by sense amplifier 136, then sense amplifier provides an appropriate signal to control processor 130 of such sensed intrinsic event. If no valid intrinsic events are sensed during a prescribed time period, referred to generally as "escape interval," then control processor 130 signals pulse generator to generate a stimulation pulse. If a valid intrinsic event is sensed before escape interval times out, control processor responds by resetting escape interval, thereby preventing pulse generator from generating a stimulation pulse. In this manner, stimulator provides stimulation pulses only when needed, e.g., Only when a valid intrinsic event is not sensed.

Control processor 130, which may be a microprocessor or equivalent processing circuit, operates in accordance with a control program that is stored in stimulator memory 140. Also stored in memory is a set of control parameters that are used by control program as it defines operation of processor. That is, control parameters define various variables associated with operation of stimulator, such as duration of escape interval, frequency, interpulse interval, duration, amplitude and relative timing parameter for each of stimulation pulses and like. Clock circuit 138 provides necessary clock signals for operation of control processor 130. Control program specifies particular order or sequence of events that are carried out by processor. For example, control program may specify that, upon detecting a valid intrinsic event, a control parameter stored in a particular address in memory should be retrieved in order to define an appropriate corresponding delay. Control program may further specify that if a further valid intrinsic event is sensed before delay times out, then another control parameter stored in another location (address) of memory 40 should be retrieved in order to define an appropriate delay. If a valid intrinsic event is not sensed before timing out of delay, then control program may specify another memory address where a control parameter is stored that defines amplitude and pulse width of a stimulation pulse train that is to be generated.

Of course, above example is extremely simple, but it illustrates basic operation of stimulator. Those skilled in art will recognize that there are numerous events associated with gastrointestinal cycle, and that re are numerous types of cycles that may occur. Control program, in combination with other control circuitry within stimulator, thus define how stimulator responds to each possible event and intrinsic cycle type. Control parameters, in turn, define magnitude of variables associated with such response, e.g., Duration of time periods, amplitude and widths of stimulation pulses, gain of amplifiers, threshold level of threshold detectors, and like.

In order to add flexibility to operation of stimulator 20, stimulator also includes a telemetry circuit 142. Telemetry circuit 142 allows access to memory 140 from a remote location, e.g., From an external programmer 146 at a non-implanted location. External programmer 146 includes means for establishing a telemetry link 144 with telemetry circuit 142 of implanted stimulator. Through this telemetry link 144, control parameters may be sent to telemetry circuit 142 for storage in memory 140. Such control parameters may thereafter be used by control program stored in memory 140 to steer operation of stimulator 120, as explained above. Additional details associated with design and operation of a telemetry circuit 142, as well as an external programmer 146, may be found in U.S. Pat. Nos. 4,809,697 and 4,944,299, incorporated herein by reference.

External programmer 146 is used to programmably set control parameters associated with operation of control processor 130. In contrast to control program, which preferably is fixed, certain control parameters that define variables used by control program (or equivalent circuitry) in controlling stimulator may be readily changed, from time to time, after implantation by using external programmer 146. Thus, should there be a need to change a given control parameter, e.g., Stimulation pulse amplitude generated by output amplifier 134, sensitivity (threshold setting) of sense amplifier 136, or other variables, then appropriate control parameters that define such variables are simply updated (programmed) through telemetry link established by external programmer 146. Such programming of control parameters is limited, however, so that associated variables can only be changed within certain safe limits that are defined by control program and/or o circuitry within stimulator.

Memory is preferably a RAM-type memory which has both a control program and a set of control parameters stored rein at respective memory locations (addresses). Like conventional programmable stimulators, set of control parameters in memory 140 may be selectively updated (programmed), as needed, through use of external programmer 146. Control program stored in memory 40 may also be updated, using appropriate safeguards, through use of external programmer 146. Thus, when new features requiring a new control program are added to stimulator, a patient having an existing implanted stimulator can receive benefits of such new features by simply upgrading control program stored in his or her implanted stimulator. In this manner, system permits an existing control program stored in an implanted stimulator to be non-invasively upgraded to a new version of control program.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. An apparatus for providing stimulation to the gastrointestinal tract, comprising:
   a housing,
   means for sensing electrical activity of the gastrointestinal tract between approximately 1 and 15 cycles/minute (0.017–0.25 Hz) positioned within the housing,
   a controller positioned within the housing, the controller coupled to the means for sensing,
   means for generating electrical stimulation pulse trains, the means for generating electrical stimulation pulse trains coupled to the controller and positioned within the housing; and
   means for electrically coupling the means for generating to a gastrointestinal tract of a patient.

2. The apparatus of claim 1, further comprising a signal processor and a zero-level detector, the signal processor comprising a bandpass amplifier responsively coupled to the electrical activity sensing means, the bandpass amplifier producing a bandpass filtered signal from the sensed signal; the zero-level detector being coupled to the bandpass amplifier to produce a pulse train of a frequency component proportional to the highest amplitude spectral component of the bandpass signal.

3. The apparatus of claim 1, further comprising means for recording the intrinsic gastrointestinal electrical activity for a preset period of time in response to the generation of an abnormal electrical activity signal.

4. An apparatus for providing stimulation to the gastrointestinal tract, comprising:
   a sensor for sensing intrinsic gastrointestinal electrical activity between approximately 1 and 15 cycles/minute (0.017–0.25 Hz);
   a signal processor to process the sensed intrinsic gastrointestinal electrical activity between the frequency of approximately 1 to 15 cycles/min. (0.017–0.25 Hz) and generate an abnormal gastrointestinal electrical activity trigger signal when abnormal gastrointestinal electrical activity is sensed;
   at least one medical electrical lead;
   a pulse generator, the pulse generator being coupled to the signal processor so as to receive the abnormal gastrointestinal electrical activity trigger signal, the pulse generator being coupled to the at least one medical electrical lead, the pulse generator emitting stimulation pulse trains for a pre-set period of time in response to the abnormal gastrointestinal electrical activity trigger signal from the signal processor.

5. The apparatus of claim 4, wherein the signal processor comprises a bandpass amplifier responsively coupled to the sensor, the bandpass amplifier producing a bandpass filtered signal from the sensed signal; and
   a zero-level detector coupled to the bandpass amplifier to produce a pulse train of a frequency component proportional to the highest amplitude spectral component of the bandpass signal.

6. The apparatus of claim 4, further comprising means for recording the intrinsic gastrointestinal electrical activity for a preset period of time in response to the generation of an abnormal electrical activity signal.

7. An apparatus for providing stimulation to the gastrointestinal tract, comprising:
   a sensor for sensing intrinsic gastrointestinal electrical activity between approximately 1 and 15 cycles/minute (0.017–0.25 Hz);
   a signal processor to process the sensed intrinsic gastrointestinal electrical activity between approximately 1 and 15 cycles/minute (0.017–0.25 Hz) and generate an abnormal gastrointestinal electrical activity trigger signal when abnormal gastrointestinal electrical activity is sensed;
   a pulse generator, the pulse generator coupled to the signal processor so as to receive the abnormal gastrointestinal electrical activity trigger signal, the pulse generator coupled to at least one medical electrical lead, the pulse generator emitting stimulation pulse trains only during the time the abnormal gastrointestinal electrical activity trigger signal is received.

8. The apparatus of claim 7, wherein the signal processor comprises a bandpass amplifier responsively coupled to the sensor, the bandpass amplifier producing a bandpass filtered signal from the sensed signal;
   a zero-level detector coupled to the bandpass amplifier to produce a pulse train of a frequency component proportional to the highest amplitude spectral component of the bandpass signal.

9. The apparatus of claim 7 further comprising means for recording the intrinsic gastrointestinal electrical activity for a preset period of time in response to the generation of an abnormal electrical activity signal.

10. An apparatus for providing on-demand stimulation of the gastrointestinal tract comprising:
    a housing, the housing having means for detecting cyclic activity of smooth muscle;
    means for processing the detected cyclic activity of smooth muscle greater than approximately 10 cycles per minute or less than approximately 1 cycle per minute, the means for processing emitting an abnormal gastrointestinal activity signal when the cyclic activity of smooth muscle greater than approximately 10 cycles per minute or less than approximately 1 cycle per minute is processed;
    means for generating electrical stimulation in response to the abnormal gastrointestinal activity signal;
    means for electrically coupling the means for generating to a gastrointestinal tract of a patient wherein the means for processing the detected cyclic activity of smooth muscle processes the detected cyclic activity of smooth muscle which is greater than approximately 10 cycles per minute or less than approximately 2 cycles per minute.

11. The apparatus of claim 10 further comprising means for detecting cyclic activity of smooth muscle; means for processing the detected cyclic activity of smooth muscle greater than approximately 10 cycles per minute or less than approximately 1 cycle per minute, the means for processing emitting an abnormal gastrointestinal activity signal when the cyclic activity of smooth muscle greater than approximately 10 cycles per minute or less than approximately 1 cycle per minute is processed; and means for emitting electrical stimulation in response to the abnormal gastrointestinal activity signal.

* * * * *